(12) United States Patent
Bradaczek et al.

(10) Patent No.: US 7,285,168 B2
(45) Date of Patent: Oct. 23, 2007

(54) METHOD AND APPARATUS FOR THE MEASUREMENT, ORIENTATION AND FIXATION OF AT LEAST ONE SINGLE CRYSTAL

(75) Inventors: Hans Bradaczek, Berlin (DE); Hans Berger, Berlin (DE); Hartmut Schwabe, Halle (DE)

(73) Assignee: EFG Elektrotechnische Fabrikations-und Grosshandelsgesellschaft mnB, Berlin (DE)

( * ) Notice: Subject to any disclaimer, the term of this patent is extended or adjusted under 35 U.S.C. 154(b) by 346 days.

(21) Appl. No.: 11/003,578

(22) Filed: Dec. 3, 2004

(65) Prior Publication Data

US 2006/0032430 A1    Feb. 16, 2006

(30) Foreign Application Priority Data

Aug. 10, 2004 (DE) .............. 10 2004 039 244

(51) Int. Cl.
*C30B 13/34* (2006.01)
*C30B 35/00* (2006.01)

(52) U.S. Cl. .................. 117/69; 117/201; 117/202; 117/902

(58) Field of Classification Search .............. 117/69, 117/201, 202, 902, 2, 3, 13
See application file for complete search history.

(56) References Cited

U.S. PATENT DOCUMENTS

| | | | |
|---|---|---|---|
| 3,870,880 A | 3/1975 | Merigoux et al. | |
| 4,412,345 A | 10/1983 | Workman et al. | |
| 4,771,446 A | 9/1988 | Howe et al. | |
| 4,788,702 A | 11/1988 | Howe et al. | |
| 5,839,424 A | 11/1998 | Hauser | |
| 5,904,136 A | 5/1999 | Nagatsuka et al. | |

FOREIGN PATENT DOCUMENTS

| | | |
|---|---|---|
| DE | 697 21 115 | 3/1997 |
| DE | 197 23 083 | 6/1997 |
| EP | 0 245 923 | 3/1987 |
| EP | 0 802 029 | 10/1997 |
| JP | 57136150 | 8/1982 |
| WO | WO 00/06999 | 2/2000 |

OTHER PUBLICATIONS

Patent Abstracts of Japan; Publication No. 09-033456 published Feb. 7, 1997 (Appln No. 07-207372 Jul. 24, 1995, Rigaku Corp.).

*Primary Examiner*—Felisa Hiteshew
(74) *Attorney, Agent, or Firm*—Reed Smith LLP

(57) ABSTRACT

For the measurement, orientation and fixation of at least one single crystal, it is the object of the invention to ensure increased accuracy in the determination of crystallographic orientation and oriented fixation regardless of the outer geometry of the single crystals, and the fixation should guarantee a highly accurate cutting also with very hard materials such as sapphire or silicon carbide. The single crystal is adjustably positioned on a revolving table for determining the crystal lattice orientation, wherein the crystal lattice orientation is determined during at least one revolution of the revolving table based on a plurality of x-ray reflections. The orientation of the crystal lattice is carried out with reference to the determined angles of the normal of the lattice plane relative to the axis (X-X) of the revolving table as reference direction before carrying out the fixation of the single crystal and the fastening on a support oriented in reference direction. By virtue of the invention, a plurality of single crystals can be oriented, fixated, stacked one on top of the other and connected to one another and subsequently connected simultaneously to a common support. Further, the invention makes it possible to monitor the orientation of every single crystal after fastening to the common support.

11 Claims, 4 Drawing Sheets

METHOD AND APPARATUS FOR THE MEASUREMENT, ORIENTATION AND FIXATION OF AT LEAST ONE SINGLE CRYSTAL

CROSS-REFERENCE TO RELATED APPLICATION

This application claims priority of German Application No. 10 2004 039 244.7, filed Aug. 10, 2004, the complete disclosure of which is hereby incorporated by reference.

BACKGROUND OF THE INVENTION a) Field of the Invention

The invention relates to a method for the measurement, orientation and fixation of at least one single crystal and an apparatus directed thereto.

b) Description of the Related Art

It is well known that single crystals must be severed along cutting planes having a given orientation to the coordinate axes of the crystal lattice for application in the semiconductor industry and optics industry.

It has already been recognized that the determination of crystal orientation required for this purpose, i.e., the relationship of the crystallographic axes to the geometric axes and the given positioning of the single crystals relative to the cutting plane of a cutting device, e.g., a wire saw, outside of this device affords considerable advantages.

It is known, for example, from EP 0 802 029 B1 to fixedly arrange a plurality of circular-cylindrical single crystals successively in alignment with one another on a cutting support outside of the cutting device by means of a rotationally and translationally adjustable receiving device in such a way that the single crystals can be cut simultaneously in defined directions relative to the crystal lattice by means of the cutting device.

However, when very hard single crystals, e.g., sapphire or silicon carbide, are to be prepared by the device for simultaneous cutting in a multiple wire saw, a device of this kind is poorly suited because faulty cutting can result when the cutting wires pass through the free spaces remaining between the single crystals that are fastened to the cutting support due to tensions occurring in individual cutting wires.

Further, it is disadvantageous that the suggested method and the device depend on the measured single crystals being in fact arranged on the cutting support with the required accuracy. At least subsequent checking is ruled out because, after they are fixed on the support, the single crystals lying on the inside are no longer accessible to the end face measurement provided for the single crystals.

Another problem consists in that the x-ray diffractometer, which is normally used to determine crystal orientation and by means of which, e.g., according to JP 09-033456 A, the orientation of two lattice planes is determined one after the other by a theta scan, cannot work with the accuracy required for certain applications. One reason for this is that the required absolute relationship between the two measurements cannot be produced with sufficient accuracy.

Some of the applications in which the required cutting accuracy is appreciably higher than that required in silicon chip fabrication, for example, are the manufacture of white light emitting diodes, which are already being used in headlights for motor vehicles and will someday also be able to replace incandescent and fluorescent lamps, and the manufacture of light emitting diodes for data storage which emit in the blue and ultraviolet spectra. When sapphire or silicon carbide are to be used as substrates for producing components in this way, an increased accuracy of the surface orientation is crucial for the growth quality of the functional layers, generally based on gallium nitride, due to the required heteroepitaxy.

OBJECT AND SUMMARY OF THE INVENTION

Therefore, it is the primary object of the invention to ensure increased accuracy in the determination of crystallographic orientation and aligned fixation regardless of the outer geometry of the single crystals, and the fixation should guarantee a highly accurate cutting also with very hard materials such as sapphire or silicon carbide.

According to the invention, this object is met by a method for the measurement, orientation and fixation of at least one single crystal, wherein the single crystal is adjustably positioned on a revolving table for determining the crystal lattice orientation and angles of the lattice plane normal relative to the axis of the revolving table are determined during at least one revolution of the revolving table based on x-ray reflections, and wherein the orientation of the single crystal is carried out based on the determined angles relative to the axis of the revolving table serving as reference direction before carrying out the fixation of the single crystal and the fastening on a support oriented in reference direction.

The single crystal is preferably positioned on the revolving table so as to be tiltable around two tilt axes in such a way that the intersection of the tilt axes serves as a reflection point for an x-ray beam by which reflections are generated at a plurality of lattice planes for determining the angles when the single crystal positioned on the revolving table is rotated.

When two or more single crystals with identical or different orientation are to be machined simultaneously in a machine or installation provided for further processing, a particular embodiment of the invention consists in that a plurality of single crystals are positioned successively one above the other to form a stack, are measured, oriented in a defined manner and fixated, and the stacked single crystals are subsequently simultaneously fixedly connected to the support which is oriented in the reference direction.

The fixed orientation of the individual single crystals can be checked and, in case of any deviations from a reference orientation, a new orientation and fixation can be carried out.

If necessary, a suitable adhesive is introduced between adjacent single crystals before the definitive fixation in order to fill the gap between the single crystals and enable a stable stack with a view to subsequent machining steps.

For this purpose, an adhesive layer can be applied to a single crystal that is already fixated in an oriented manner and another single crystal that is provided for forming a stack can be placed on the adhesive layer prior to measurement, orientation and fixation. The hardening time of the adhesive should exceed the time period for measurement, orientation and fixation of the additional single crystal.

Further, the invention can be constructed in such a way that an auxiliary support serving to connect to the common support is arranged in crystallographic orientation at each single crystal prior to positioning.

In comparison to known solutions, the invention achieves an orientation accuracy that is improved by an order of magnitude when the single crystals are glued to a support.

The invention advantageously permits the results of the gluing to be monitored in that the single crystals connected to the common support are checked with respect to the crystal lattice orientation that is actually achieved by means of suitable x-ray reflections at a crystal face approximately perpendicular to the original crystal face serving as measurement surface. For this purpose, the stack of single crystals that is fixed on the support is positioned so as to be displaceable with its stack direction perpendicular to the axis of the revolving table, so that the reflection point can be located on a single crystal to be measured.

The method according to the invention makes it possible to measure at different suitable lattice planes from any geometric positions, and single crystals of any shape and type can be oriented and fixated because the single crystals remain in the apparatus and measurement and orientation rely only on purely crystallographic parameters.

Accordingly, it is not important whether the single crystal is in wafer shape or is shaped as a circular or square cylinder (ingot) or whether or not a geometric axis can be defined. An (outwardly) completely irregular single crystal can also be measured, oriented and fixated.

The measurement data are recorded during an entire measurement period (e.g., during a continuous or stepwise 360-degree rotation of the single crystal). The required measurement accuracy can be achieved by selecting either the rotating speed during the measurement or the measurement time per measurement step or by accumulating measurement data over a number of measurement periods.

Further, the above-stated object is met according to the invention by an apparatus for the measurement, orientation and fixation of at least one single crystal, containing a revolving table with a receptacle for at least one crystal holder having an adjusting and fixating device for orienting the crystal lattice of a single crystal relative to the axis of the revolving table as reference direction and for orientated fixation of the single crystal, an arrangement of an x-ray source and a detector, which arrangement is vertically adjustable relative to the revolving table and by means of which angles of the normal of the lattice plane of the single crystal relative to the axis of the revolving table are determined during at least one revolution of the revolving table, wherein the determined angles are used to calculate adjusting values for the adjusting and fixating device for orientation of the crystal lattice of the single crystal, and an adjusting device for a support serving to receive at least one single crystal that is fixated in an oriented manner, which adjusting device operates so as to be directed perpendicular to the axis of the revolving table.

The crystal holder comprises an outer frame with a gimbal-suspended inner holder frame for the single crystal and adjusting means for adjusting and fixating the single crystal that is clamped in the inner holder frame. Further, a horizontal guide is provided for the adjusting means in the outer frame.

In a particularly advantageous manner, the apparatus is suitable for checking the accuracy achieved in the oriented fixation in that a linear guide with a guide direction running perpendicular to the axis of the revolving table is provided for receiving the support on the revolving table with the at least one single crystal that is fixated in an oriented manner.

The invention will be described more fully in the following with reference to the schematic drawings.

DESCRIPTION OF THE PREFERRED EMBODIMENTS

Figure 1:
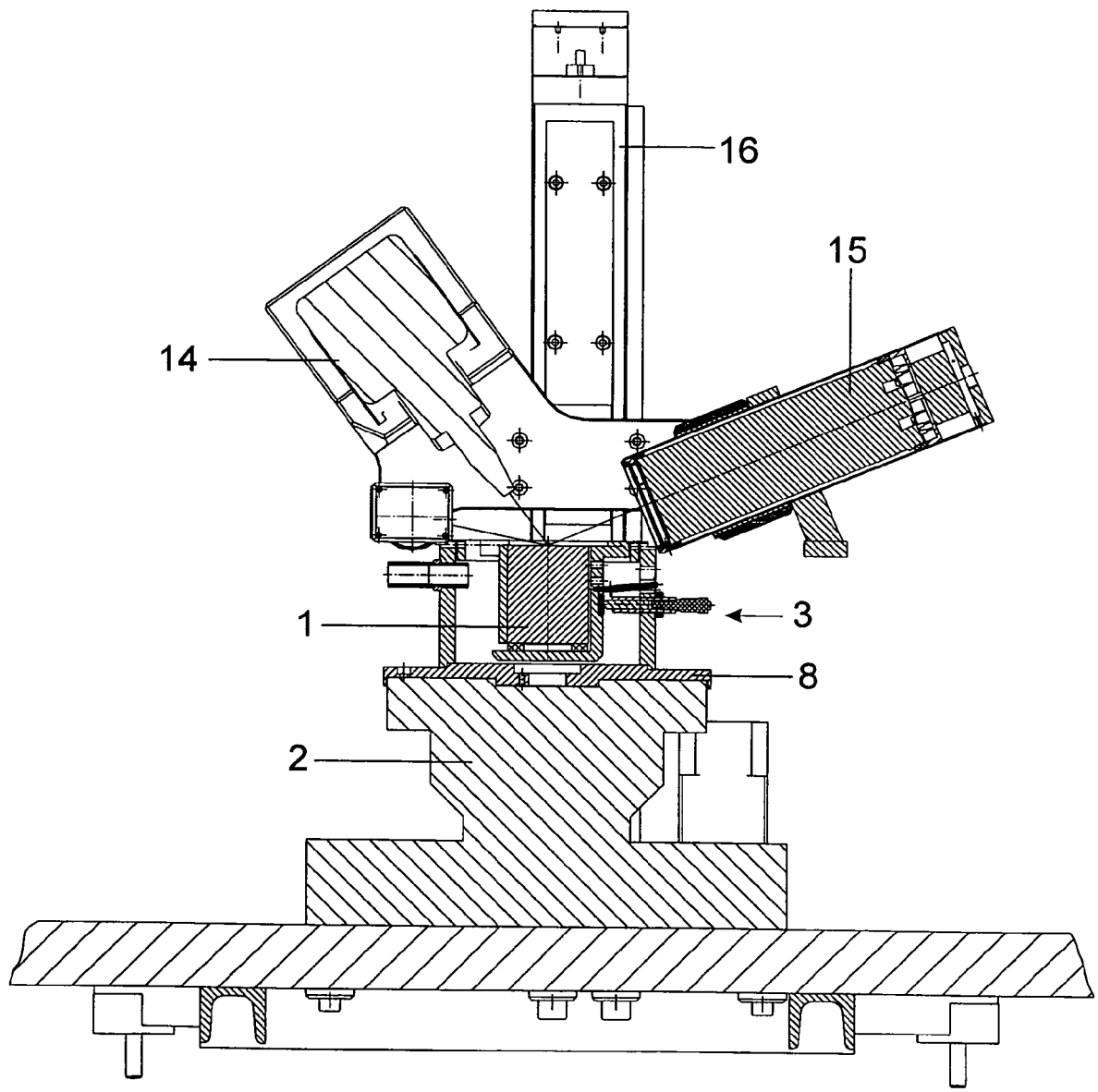
FIG. 1 shows an apparatus, according to the invention, for the orientation and oriented fixation of at least one single crystal.
Figure 2:
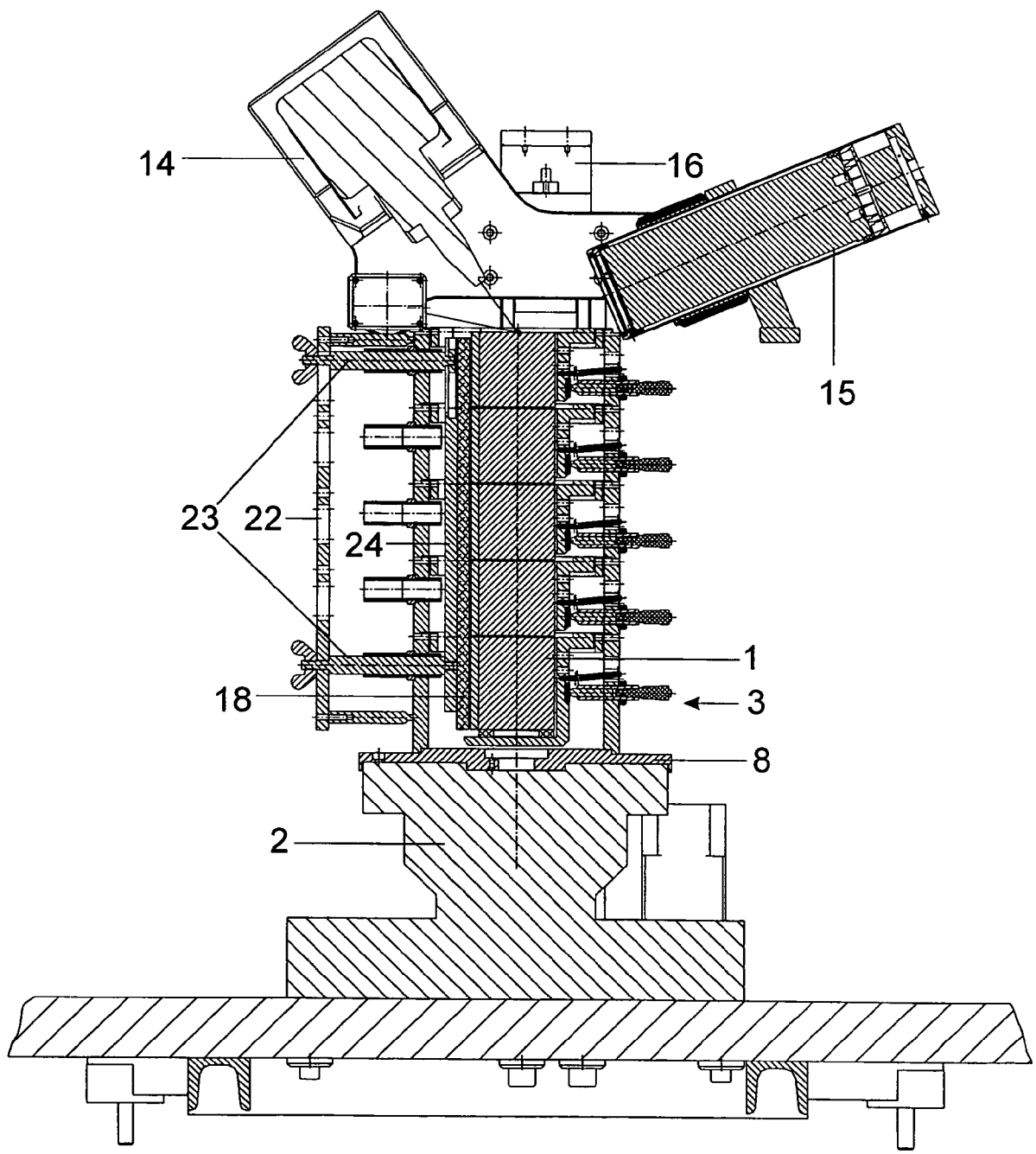
FIG. 2 shows the apparatus, according to FIG. 1, in which a plurality of single crystals are stacked one on top of the other and connected to a common support.
Figure 3:
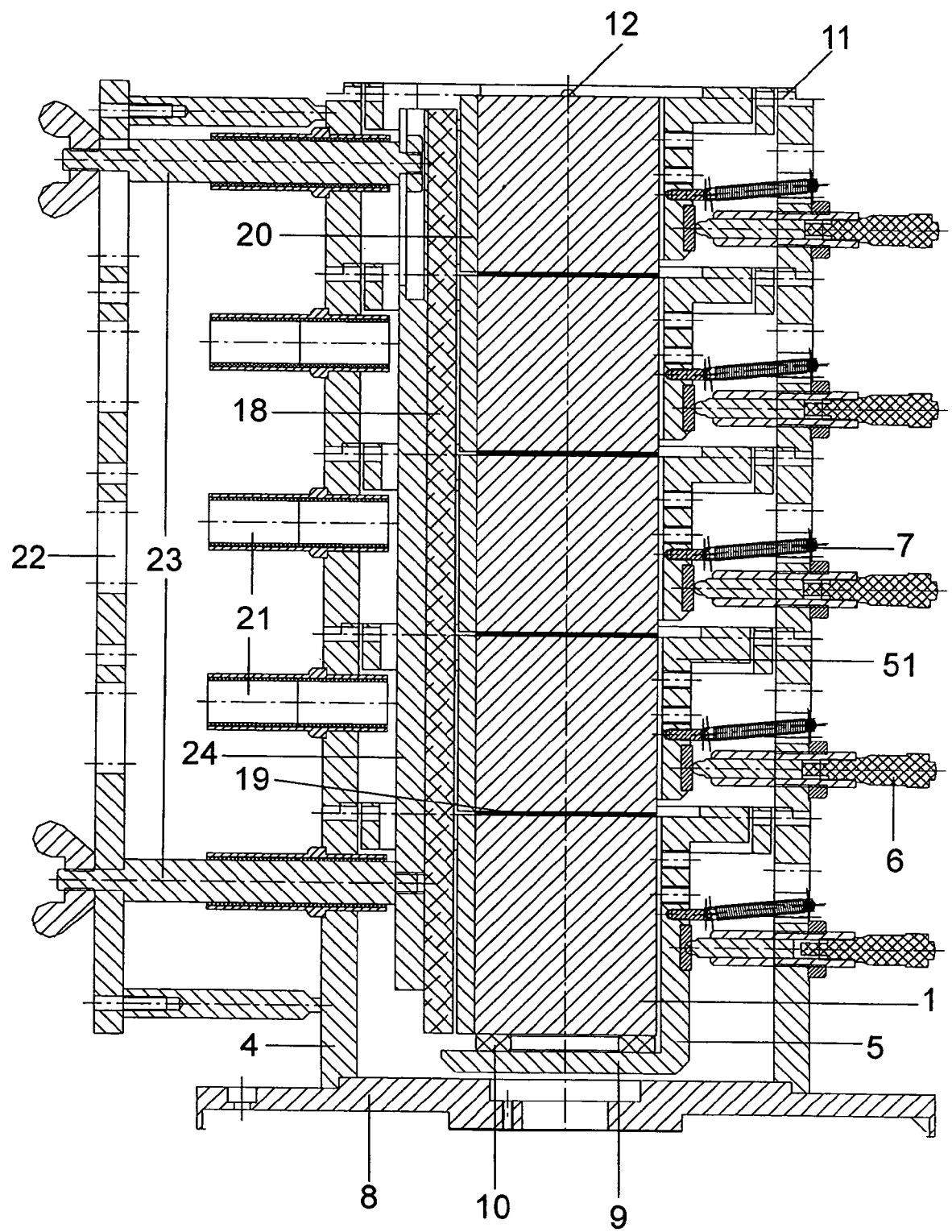
FIG. 3 shows an apparatus for advancing a support to a composite of stacked single crystals.

The apparatus shown in FIGS. 1 and 2 has a revolving table 2 which is used for individual measurement of a single crystal 1 or particularly for successively measuring a plurality of single crystals 1 (in this case, circular-cylindrical ingots, for example) to be stacked one on top of the other and which is characterized by high synchronous running values and low axial wobble. A crystal holder 3 is provided for every single crystal 1, which is already cut approximately parallel to the provided cutting plane. The crystal holder 3, according to FIG. 3, comprises an outer frame 4 with a gimbal-suspended inner holder frame 5 for the single crystal 1 and adjusting screws 6 with counter-springs 7 as an adjustable adjusting device for aligning and fixating the single crystal 1 which is attached to the inner holder frame 5.

The inner holder frame 5 of the crystal holder 3, which is fixedly connected at the very bottom to the outer frame 4 by a receptacle 8 on the revolving table 2, has a base 9 as support for a first single crystal 1. Insertable intermediate bases 10 make it possible to adapt the height of the single crystal 1 so that the single crystal 1 is positioned so as to be rotatable around two tilt axes 11, 12 (12 extends perpendicular to the drawing plane), which are preferably directed perpendicular to one another, in such a way that the intersection of the tilt axes 11, 12 serves as a reflection point for an x-ray beam 13 which is preferably provided for measurement.

The construction of the crystal holder 3 accordingly ensures that the single crystal 1 can be adjusted in any way without changing the point of incidence of the x-ray 13 on its surface so as to change the reflection point.

An x-ray source 14 for generating the x-ray beam 13 and a detector 15 for receiving a succession of x-ray reflections from a plurality of lattice planes of the single crystal 1 during at least one revolution of the revolving table 2 are fixedly oriented with respect to one another taking into account the Bragg angle of the lattice planes to be measured and their inclination relative to the crystal surface and are supported on a vertically directed linear guide 16 for adapting the height of the reflection point. A detector window 17 (FIG. 4) is provided with a lead mask which is designed in such a way that only the desired reflections R are measured. An optical system serves to automatically regulate the required height relative to the revolving table 2.

Figure 4:
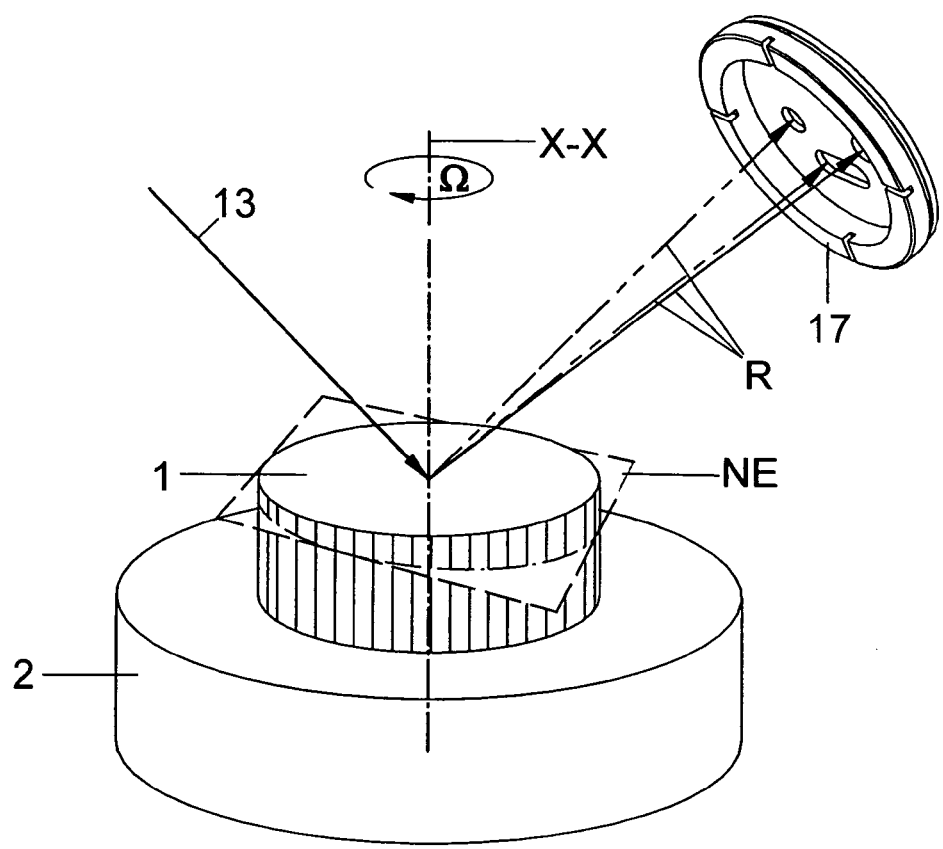
FIG. 4 is a diagram illustrating the measurement process used in the invention for determining a lattice plane angle.

In the method according to the invention, the determination of the lattice plane angle, i.e., the deviation of the position of the normal line on the lattice plane NE to the axis X-X of the revolving table 2, is carried out, as is illustrated in FIG. 4, with the revolving table 2 revolving at a constant speed or step-by-step, by measuring at a lattice plane NE whose normal is inclined at an angle $\epsilon$ to the axis of the revolving table 2 in that the x-ray beam 13 is radiated at angle δ deviating from the angle $\Theta_B+\epsilon$, that is, at angle $\Theta_B+\epsilon-\delta$ ($\Theta_B$ ... Bragg angle). As a result, the lattice plane NE used for measurement changes its inclination relative to the incident x-ray beam 13 during rotation of the revolving table 2 due to a wobbling movement, and from the angular distance $2\Omega$ of reflections occurring at certain rotational angles $+\Omega$ and $-\Omega$ the angular deviation δ of the lattice plane normal from the axis X-X of the revolving table 2 can be exactly determined within a measurement time of several seconds to several angular seconds. When the normal of the cutting plane is approximately an axis of symmetry of the crystal, e.g., a trigonal axis at (0001) sections of sapphire, approximately identical characteristics are present in this example for satisfying the reflection condition after 120°, so that three pairs of reflections occur over a full revolution.

Since the reflection positions can be measured in a periodically recurring manner with repeated revolutions of the revolving table 2, averages can advantageously be taken so that an increase in accuracy results compared with static measurement methods such as the theta scan.

The tilt angles around the tilt axes 11, 12 of the gimbal suspension are calculated from the determined lattice plane angles with special software in such a way that an orientation can be carried out relative to the coordinate system of the apparatus, particularly with respect to the axis X-X of the revolving table 2 as reference direction, by means of the adjusting device. The coordinate system of the apparatus has, in addition, a defined orientation to that of the cutting device. Both are preferably directed in the same direction.

The adjusting values can be transmitted to the adjusting device either manually or automatically by means of corresponding drives, not shown, e.g., actuating motors or piezo-actuators.

After the orientation of the single crystal 1 relative to the axis X-X of the revolving table 2 is carried out, this orientation is fixed by means of the adjusting device.

If necessary, the fixed orientation can be checked again with the described measuring methods and changed, as the case may be.

The device according to the invention is suitable particularly for preparing a plurality of single crystals 1 for simultaneous cutting in a cutting device such as a multiple wire saw. Since the single crystals 1 do not usually reach the dimensions required for optimally filling the wire saw for technical reasons relating to manufacture, it is common to fixate a plurality of single crystals in such a way that they are oriented to one another so as to move them into the wire saw together and orient them to the coordinate system of the wire saw.

Therefore, according to the invention, a plurality of single crystals 1 are positioned one above the other individually in succession to form a stack, measured, fixated and subsequently, after achieving the required stack height, simultaneously fixedly connected to a common support 18 which realizes the orientation in the cutting device.

Like the bottommost single crystal 1 positioned on the revolving table 2, each of the additional single crystals 1 is attached in a crystal holder 3 which, in contrast to the crystal holder 3 of the first single crystal 1, has an inner holder frame 51 without a bottom, so that every additional single crystal 1 is directly adjacent to a single crystal 1 that has been fixated in an oriented manner previously.

The stack of single crystals 1 is carried out in such a way that the crystal holders 3 with the outer frame 4 are placed one on top of the other and fixedly connected to one another so as to produce the reference to the axis X-X of the revolving table 2. After another crystal holder 3 has been placed on a crystal holder 3 with a single crystal 1 that has been fixated in an oriented manner previously, the determination of the lattice plane angles, the orientation and the fixation of the other single crystal 1 takes place in the manner described above after the x-ray source 14 and detector 15 are raised into a higher position so that the x-ray beam 13 is directed to another single crystal 1.

When the single crystals 1 are particularly hard crystal material such as sapphire or silicon carbide, an adhesive layer 19 can be applied between adjacent single crystals 1 in order to fill the gap between the single crystals 1 and form a stable stack. Changing wire tensions in cutting wires running adjacent to a cutting wire penetrating into a gap and faulty cuts resulting from this during sawing can be prevented in this way.

The required adhesive is applied to the single crystal 1 that is already fixated in an oriented manner, the additional single crystal 1 that has not yet been measured or fixated in oriented manner being placed in this adhesive layer with a certain pre-direction. The hardening time of the adhesive is selected in such a way that it exceeds the time required for measurement, orientation and fixation of the additional single crystal 1.

After the additional single crystal 1 is measured, oriented and fixated, the adhesive can harden. However, this can also take place during the placement, measurement, orientation and fixation of additional single crystals 1 because each of the single crystals 1 is fixated in its crystal holder 3.

For simultaneous connection of the single crystals 1 to the common support 18, it is advantageous when an auxiliary support 20 is arranged, e.g., by gluing, in a crystallographically oriented manner at every single crystal before fastening in the crystal holder 3. The auxiliary support 20, whose longitudinal extension does not exceed that of the single crystal 1, is shaped corresponding to the outer surface area of the single crystal 1 and its side opposite from the shaped portion forms a sufficiently large gluing surface in relation to the support.

An often desirable orientation of a determined crystal axis in the forward feed direction when sawing can be effected by means of suitable arrangement of the auxiliary supports 20. In order to determine and mark the gluing locations, an x-ray measurement of the same kind is taken at the single crystal 1 which simply lies on the revolving table 2. Gluing is carried out outside of the apparatus.

Further, appropriate guides 21 and a gluing crosspiece 22 are provided for simultaneous connection of the single crystals 1 to the common support 18 in the outer frame 4. An adjusting device 23 supported by the guides 21, acting perpendicular to the axis X-X of the revolving table 2, lightly presses the support 18 held by a magnetic strip 24 against the auxiliary supports 20 which are arranged in a row. The inner holder frames 5 have cutouts (not shown) which are in alignment with one another and in which the support 18 penetrates so that it can also reach the auxiliary supports 20.

Since the gluing surfaces of the auxiliary supports 20 do not generally extend exactly parallel to one another, the surface of the common support 18 used for the connection of the single crystals 1 has compensating foam-like material which is impregnated with a glue. After the glue hardens, the single crystal stack can be removed and moved into a receptacle of the wire saw because of the precise design of the support 18, so that the crystal lattice is oriented in the desired manner relative to the cut direction.

Before this, however, the substantial advantage of the invention can also be used to check once more the interconnected single crystals 1 for the orientation of the desired cut direction to the crystal lattice that is actually achieved.

Figure 5:
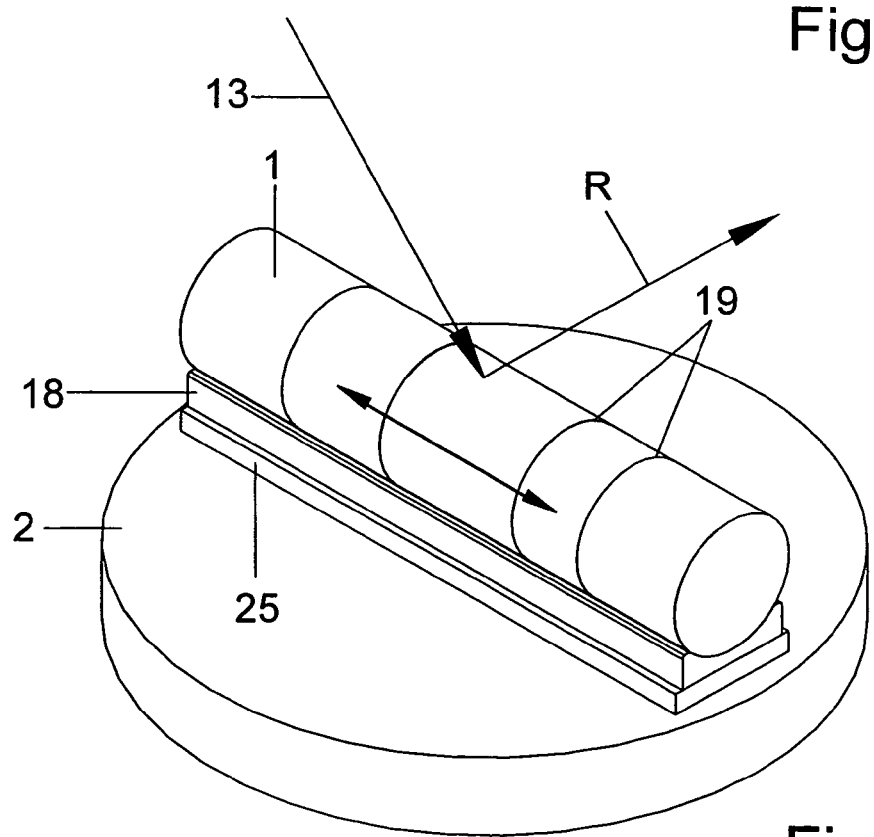
FIG. 5 shows the arrangement for a composite of stacked single crystals on the revolving table for checking the orientation of the individual single crystals.

For this purpose, the common support 18 with the single crystals 1 according to FIG. 5 is arranged on a linear guide 25 which is located on the revolving table 2 and whose guide direction extends perpendicular to the axis X-X of the revolving table 2. X-ray reflections at lattice planes extending at suitable angles to the axis of rotation are selected for measurement. The x-ray beam 13 is directed to the single crystal 1 to be measured in that the support 18 is displaced horizontally (arrow direction=stack direction) in the event that a change in the orientation of the x-ray source 14 and detector 15 relative to one another is necessary.

When the measurement shows that the adjusted cutting planes of every single crystal 1 with reference to the crystal lattice extend parallel to the axis X-X of the revolving table 2 and perpendicular to the displacement direction, the gluing has been carried out with the required high accuracy without tilting of the crystals.

While the foregoing description and drawings represent the present invention, it will be obvious to those skilled in the art that various changes may be made therein without departing from the true spirit and scope of the present invention.

What is claimed is:

1. A method for the measurement, orientation and fixation as well as fastening of at least one single crystals on a common support, comprising the steps of:
    adjustably and successively positioning the single crystals individually arranged in stackable crystal holders on a revolving table for determining the crystal lattice orientation and determining angles of the lattice plane normal relative to the axis of the revolving table during at least one revolution of the revolving table based on x-ray reflections; and
    successively carrying out the orientation of the single crystal based on the determined angles of coordinates of the crystal lattice relative to the axis of the revolving table serving as reference direction before the orientation and the fixation of the single crystals in the stackable crystal holders and carrying out simultaneous fastening of stacked, measured, oriented and fixed single crystals on the common support oriented in reference direction.

2. The method according to claim 1, wherein the single crystals are positioned on the revolving table so as to be adjustable around two tilt axes in such a way that the intersection of the tilt axes serves as a reflection point for an x-ray beam by which reflections are generated at a plurality of lattice planes of the single crystals for determining the angles of coordinates of the crystal lattice relative to the axis of the revolving table when the single crystals positioned on the revolving table are rotated.

3. The method according to claim 2, wherein x-ray reflections are generated at a plurality of lattice planes of the single crystals during a measurement.

4. The method according to claim 2, wherein the fixated orientation is checked and an orientation and fixation is carried out again in case of any deviations from a reference orientation.

5. The method according to claim 1, wherein an auxiliary support serving to connect to the common support is arranged in a crystallographically oriented manner at each single crystal prior to positioning.

6. The method according to claim 1, wherein the single crystals connected to the common support are checked with respect to the crystal lattice orientation that is actually achieved by means of suitable x-ray reflections at a crystal face approximately perpendicular to the original crystal face serving as measurement surface.

7. The method according to claim 6, wherein, in order to check the orientation of the desired cut direction relative to the crystal lattice, the stack of single crystals is positioned so as to be displaceable with its stack direction perpendicular to the axis of the revolving table, so that the reflection point can be located on a single crystal to be measured.

8. An apparatus for the measurement, orientation and fixation as well as fastening of single crystals, comprising:
    a revolving table with a receptacle;
    stackable crystal holders;
    wherein said crystal holders being in a stacked manner connectable to said receptacle and having adjusting and fixating devices for orienting the crystal lattice of single crystals individually arranged in said crystal holders relative to the axis (X-X) of the revolving table as reference direction and for orientated fixation of the single crystal;
    an arrangement of an x-ray source and a detector, which arrangement is vertically adjustable relative to the revolving table and by which angles of the normal of the lattice plane of the single crystal relative to the axis (X-X) of the revolving table are determined during at least one revolution of the revolving table, the determined angles being used to calculate adjusting values for the adjusting and fixating device for orientation of the crystal lattice of the single crystal; and
    a common support oriented in a reference direction for simultaneous fastening of a plurality of stacked, measured, oriented and fixated single crystals.

9. The apparatus according to claim 8, wherein the crystal holder comprises an outer frame with a gimbal-suspended inner holder frame for the single crystal and a first adjusting device for adjusting and fixating the single crystal that is clamped in the inner holder frame.

10. The apparatus according to claim 9, wherein a horizontal guide is provided for a second adjusting device in the outer frame, which second adjusting device is provided for the common support and operates so as to be directed perpendicular to the axis of the revolving table.

11. The apparatus according to claim 8, wherein a linear guide with a guide direction running perpendicular to the axis (X-X) of the revolving table is provided for receiving the common support with the at least one single crystals fixated in an oriented manner on the revolving table.

* * * * *